(12) United States Patent
Wosnick et al.

(10) Patent No.: US 8,119,763 B2
(45) Date of Patent: Feb. 21, 2012

(54) PRODUCTION OF POLYESTERS IN A CONTINUOUS PACKED-BED REACTOR USING IMMOBILIZED ENZYME CATALYSTS

(75) Inventors: Jordan H. Wosnick, Toronto (CA); Santiago Faucher, Oakville (CA)

(73) Assignee: Xerox Corporation, Norwalk, CT (US)

( * ) Notice: Subject to any disclaimer, the term of this patent is extended or adjusted under 35 U.S.C. 154(b) by 652 days.

(21) Appl. No.: 12/240,421

(22) Filed: Sep. 29, 2008

(65) Prior Publication Data

US 2010/0081076 A1 Apr. 1, 2010

(51) Int. Cl.
*C08C 19/20* (2006.01)
(52) U.S. Cl. ........ 528/354; 528/357; 523/324; 523/500; 536/126; 526/89; 526/204
(58) Field of Classification Search .................. 536/134, 536/126; 523/412, 324, 500; 528/354, 357; 526/89, 204
See application file for complete search history.

(56) References Cited

U.S. PATENT DOCUMENTS

| | | | |
|---|---|---|---|
| 5,449,743 A * | 9/1995 | Kobayashi et al. | 528/355 |
| 6,559,275 B2 * | 5/2003 | Minami et al. | 528/354 |
| 2006/0100390 A1 * | 5/2006 | Heise et al. | 525/412 |

* cited by examiner

*Primary Examiner* — Hoa Le
(74) *Attorney, Agent, or Firm* — MH2 Technology Law Group LLP

(57) ABSTRACT

In accordance with various embodiments, there is a method of making a polyester. The method can include providing a monomer solution, the monomer solution including one or more cyclic esters in a concentration ranging from about 1 to about 100% and one or more solvents in a concentration ranging from about 99% to about 0%. The method of making a polyester can also include providing a packed-bed reactor including one or more immobilized enzymes, wherein the packed-bed reactor has an inlet and an outlet. The method can further include circulating the monomer solution through the packed-bed reactor to generate a solution enriched with polyester, such that the one or more immobilized enzymes convert the one or more cyclic esters to polyester in the packed-bed reactor during circulation and collecting the solution enriched with polyester exiting through the outlet.

11 Claims, 4 Drawing Sheets

US 8,119,763 B2

PRODUCTION OF POLYESTERS IN A CONTINUOUS PACKED-BED REACTOR USING IMMOBILIZED ENZYME CATALYSTS

FIELD OF THE INVENTION

The present invention relates to environmentally benign methods of making polyester using immobilized enzyme catalyst.

BACKGROUND OF THE INVENTION

Low-melt polyester-based toners use a combination of amorphous and crystalline polyesters to achieve low-melt behavior, enabling faster print speeds and lower energy consumption. While the melting behavior of this polyester-based toner provides advantages over polystyrene-based chemical toners in print speed, fuser life, and energy consumption, the synthesis and emulsification of the polyester resin is much more time and energy-consuming. In particular, the preparation of polyesters by polycondensation takes several days and relies on high temperatures (T>190° C.) and low pressures (p<1 mmHg) to drive the polymerization to completion. In addition, the polycondensation reaction requires an organotin catalyst that cannot be removed from the resulting resin, remaining at non-negligible levels. This residual catalyst is carried through the toner-making process and eventually makes its way to the printed page, and later to recycling or disposal facilities. In summary, this production process is environmentally unfavorable.

The benefits of using enzymatic ring-opening polymerization of lactones at atmospheric pressure and relatively low temperatures to generate crystalline polyesters suitable for use in chemical toners is known in the art. However, this process is difficult to scale-up, as in a batch reaction, a large and costly quantity of supported enzyme catalysts are needed to maintain reasonable reaction rates. Recovery and recycling of the supported enzyme catalysts is therefore critical to such enzyme based technologies to ensure the economics as well as purity of the final product. However, recovering and recycling enzyme catalysts is not straight forward in processes where these enzyme catalysts are used to make large molecules (MW>2000) due to high product fluid viscosity. In order to recover the enzyme catalysts in these processes, a large quantity of solvent is used to lower the viscosity of the product fluid such that the catalyst settles out by gravity and/or centripetal acceleration. As a result, the scale-up of such a process is impractical as it is both environmentally taxing and economically challenging. For these reasons, there are no known processes for the production of commercially important polymers that rely on the recovery and recycling of supported enzyme catalysts.

Accordingly, there is a need to overcome these and other problems of prior art to provide a practical and environmentally benign method of producing polymers using the immobilized enzyme catalysts.

SUMMARY OF THE INVENTION

In accordance with various embodiments, there is a method of making a polyester. The method can include providing a monomer solution, the monomer solution including one or more cyclic esters in a concentration ranging from about 1 to about 100% and one or more solvents in a concentration ranging from about 99% to about 0%. The method of making a polyester can also include providing a packed-bed reactor including one or more immobilized enzymes, wherein the packed-bed reactor has an inlet and an outlet. The method can further include circulating the monomer solution through the packed-bed reactor to generate a solution enriched with polyester, such that the one or more immobilized enzymes convert the one or more cyclic esters to polyester in the packed-bed reactor during circulation and collecting the solution enriched with polyester exiting through the outlet.

Additional advantages of the embodiments will be set forth in part in the description which follows, and in part will be obvious from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

As used herein, the term "immobilized enzyme" is synonymous and used interchangeably with "supported enzyme" and includes enzymes that are supported but not immobilized, i.e., enzymes that are adsorbed to the polymeric support noncovalently; enzymes that are immobilized but not supported, i.e., enzymes that are cross-linked to other enzymes; and enzymes that are both supported and immobilized.

Figure 1:
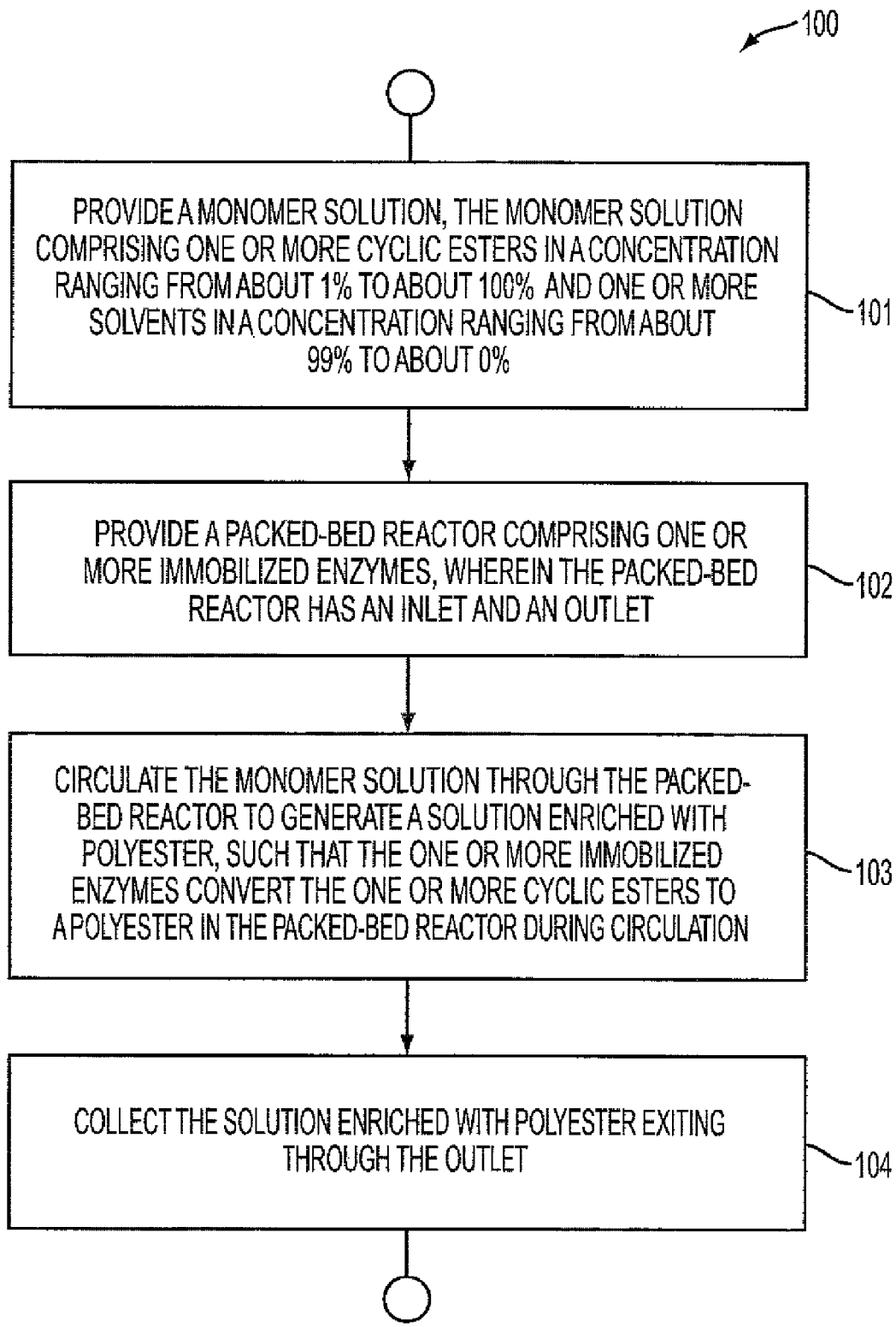
FIG. 1 shows an exemplary method of making a polyester, according to various embodiments of the present teachings.

FIG. 1 schematically illustrates an exemplary method 100 of making a polyester. The method 100 can include a step 101 of providing a monomer solution, the monomer solution including one or more cyclic esters in a concentration ranging from about 1% to about 100% and one or more solvents in a concentration ranging from about 99% to about 0%. In various embodiments, the one or more cyclic esters can include one or more 4 to 20 membered cyclic esters. In some embodiments, the one or more cyclic esters can be at least one of a pentadecalactone, a 11/12-pentadecen-15-olide (also known as a pentadecenlactone), a hexadecenlactone, and a caprolactone. In other embodiments, any suitable solvent can be used for the one or more solvents, including, but not limited to toluene; benzene; hexane and its analogues such as, for example, heptane; tetrahydrofuran and its analogues such as, for example, 2-methyltetrahydrofuran.

The method 100 can also include a step 102 of providing a packed-bed reactor including one or more immobilized enzymes, wherein the packed-bed reactor has an inlet and an outlet. In various embodiments, the packed bed reactor can be a stainless-steel tube. In some embodiments, the packed bed reactor can be a glass tube. In other embodiments, the packed bed reactor can be a polymer tubing, such as, for example, polyetheretherketone (PEEK) tubing. However, any other suitable material can be used for the packed bed reactor. The packed-bed reactor can have any suitable diameter and length. In some cases, the packed-bed reactor can have an outer diameter from about 0.1 cm to about 300 cm. In other cases, the packed-bed reactor can have a length from about 1 cm to about 300 cm and in some other cases from about 10 cm to about 100 cm. In various embodiments, the packed-bed reactor can also include one or more immobilizing agents. Exemplary immobilizing agents can include, but are not limited to a cross-linked polymeric network, cross-linked polymeric beads, polymeric packings, membranes, silica-gel, silica beads, sand, and zeolites. In various embodiments, the one or more enzymes can include any suitable lipase. Exemplary lipase can include, but are not limited to lipase PA, lipase PC, lipase PF, lipase A, lipase CA, lipase B, lipase CC, lipase K, lipase MM, and cutinase. In some cases, the packed-bed reactor can have an enzyme concentration ranging from about 0.001 g/cm$^3$ to about 0.06 g/cm$^3$ and in other cases from about 0.006 g/cm$^3$ to about 0.03 g/cm$^3$. In certain embodiments, the enzyme concentration in the packed bed reactor can be controlled by varying the ratio of the mass of enzyme to the mass of immobilizing agent.

The method 100 of making a polyester, as shown in FIG. 1 can further include a step 103 of circulating the monomer solution through the packed-bed reactor to generate a solution enriched with polyester, such that the one or more immobilized enzymes can convert the one or more cyclic esters to a polyester in the packed-bed reactor during circulation. In some cases, the packed-bed reactor is kept at a temperature from about 20° C. to about 120° C. and in other cases from about 40° C. to about 100° C. In various embodiments, the step of circulating the monomer solution through the packed-bed reactor to generate a solution enriched with polyester can include passing the monomer solution through the packed bed reactor a plurality of times. In other words, the monomer solution can be cycled through the packed bed reactor as needed. The method 100 of making a polyester can also include collecting the solution enriched with polyester exiting through the outlet, as in step 104. In various embodiments, the step of collecting the solution enriched with polyester exiting through the outlet can also include monitoring the conversion of the one or more cyclic esters to a polyester and collecting the solution enriched with polyester when the polyester has attained a substantially stabilized molecular weight or desired molecular weight. In some embodiments, the step of monitoring the conversion of the one or more cyclic esters to a polyester can include collecting and analyzing the solution enriched with polyester to determine molecular weight of the polyester in the solution. Any suitable technique can be used for the analysis of the solution enriched with polyester, such as, for example, gel permeation chromatography (GPC), differential scanning calorimetry (DSC), and nuclear magnetic resonance (NMR).

Figure 2:
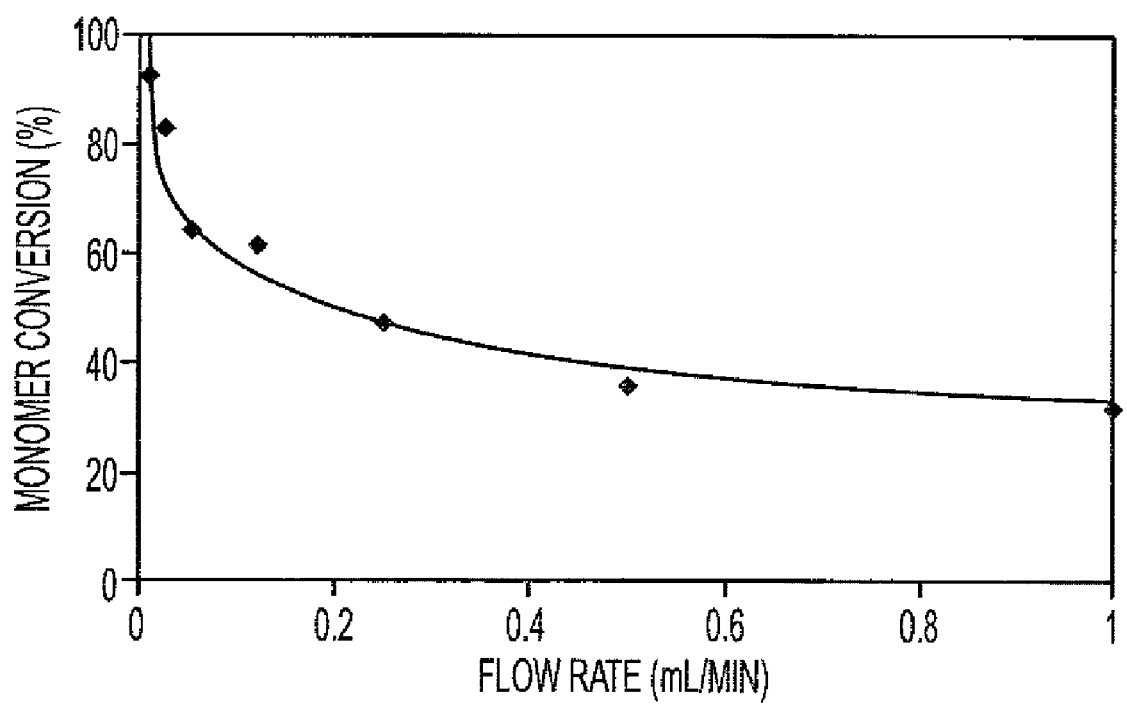
FIG. 2 shows the effect of flow rate on the monomer conversion for the exemplary polymerization of 11/12-pentadecen-15-olide, in accordance with various embodiments of the present teachings.
Figure 3:
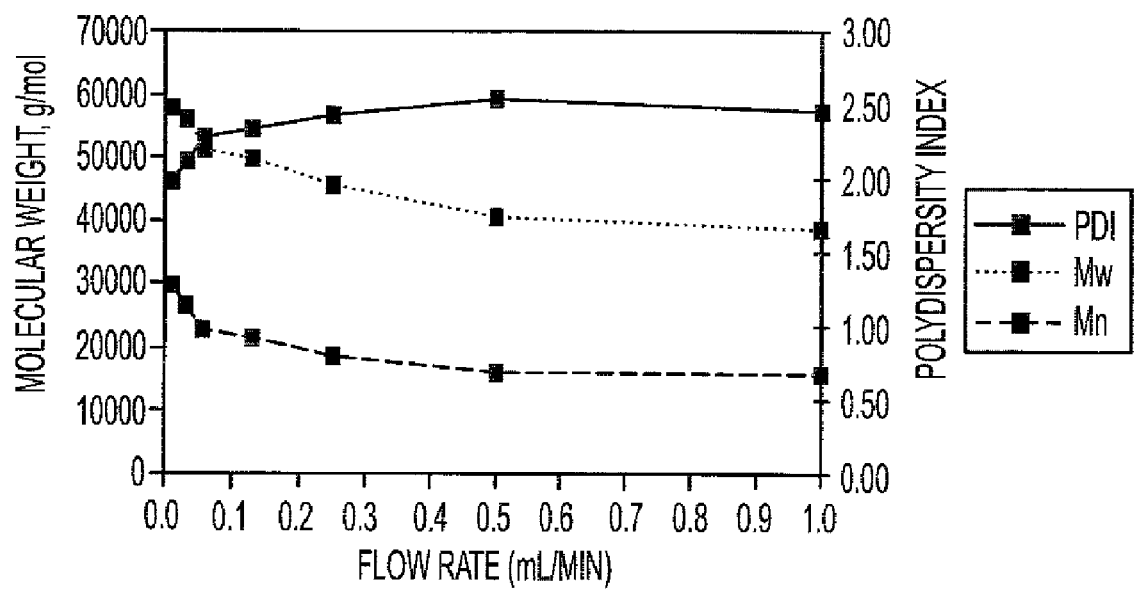
FIG. 3 shows the effect of flow rate on polymer molecular weight and polydispersity for the exemplary polymerization of 11/12-pentadecen-15-olide, in accordance with various embodiments of the present teachings.

In various embodiments, the method 100 can also include controlling one or more of molecular weight, polydispersity, and conversion ratio of the polyester using one or more of residence time of the one or more cyclic esters in the packed-bed reactor, dimensions of the packed-bed reactor, composition of the packed-bed reactor, temperature of the packed-bed reactor, and initiator concentration in the monomer solution. In certain embodiments, initiators can be water or any suitable molecule comprising one or more hydroxyl groups. Decreasing the feed rate to the reactor can cause the residence time within the reactor to increase and this in turn can cause an increase in the monomer conversion and polymer molecular weight as shown in the FIGS. 2 and 3. FIG. 2 shows the effect of flow rate on the monomer conversion for the exemplary polymerization of 11/12-pentadecen-15-olide described in Example 4. FIG. 3 shows the effect of flow rate on the polymer molecular weight and the polydispersity for the exemplary polymerization of 11/12-pentadecen-15-olide described in Example 4. As shown in FIG. 3, polydispersity of the polyester formed decreases with the flow rate to a normal distribution of 2. This is a direct result of the high rate of conversion, scission, and recombination reaction catalyzed by the enzyme that averages the molecular weight to the normal distribution.

According to various embodiments, there is a polyester resin formed by the method 100, as shown in FIG. 1. In some embodiments, there is a toner for developing an electrostatic image including a plurality of toner particles, wherein each of the plurality of toner particles can include one or more colorants and a binder resin including polyester formed by the method 100 disclosed above.

In this manner, as disclosed herein, enzymatic polyester synthesis in a packed bed reactor can provide many benefits over the same reaction in a batch process. The packed bed reactor can provide in-situ filtration as the immobilized enzyme catalyst remains in the tube during the reaction, thereby avoiding the additional step of diluting and filtering of the reaction mixture after the polymerization has completed, as in the batch process. The packed bed reactor can also have high productivity as compared to the batch reactor, as in the packed bed reactor, the reaction can be run continuously in a small space with no need to disassemble equipment for cleaning. Also, scale-up is easier and can be achieved by numbering-up or scaling-up flow reactors. The packed bed reactor can provide easy control over molecular weight and polydispersity by varying flow rate, concentration, and temperature. Furthermore energy requirements are reduced because instead of heating an entire reactor, only a small enzyme-packed tube needs to be heated. Finally, there is more efficient mixing of the reactants in the packed bed reactor as the fluid forces acting within the tube mix the reactants thoroughly and provide a fresh supply of monomers to the immobilized enzyme. Additionally, there is temperature homogeneity in the packed bed reactor as heat transfer need only occur over short distances within the narrow tube.

Examples are set forth herein below and are illustrative of different amounts and types of reactants and reaction conditions that can be utilized in practicing the disclosure. It will be apparent, however, that the disclosure can be practiced with other amounts and types of reactants and reaction conditions than those used in the examples, and the resulting devices various different properties and uses in accordance with the disclosure above and as pointed out hereinafter.

EXAMPLES

Example 1

Polymerization of 11/12-pentadecen-15-olide and Pentadecalactone in a Continuous Packed-Bed Reactor

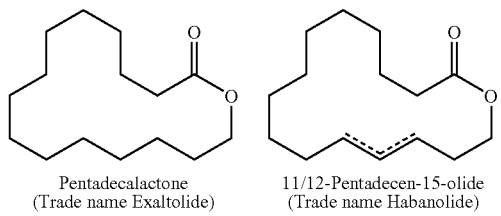

Pentadecalactone
(Trade name Exaltolide)

11/12-Pentadecen-15-olide
(Trade name Habanolide)

Figure 4:
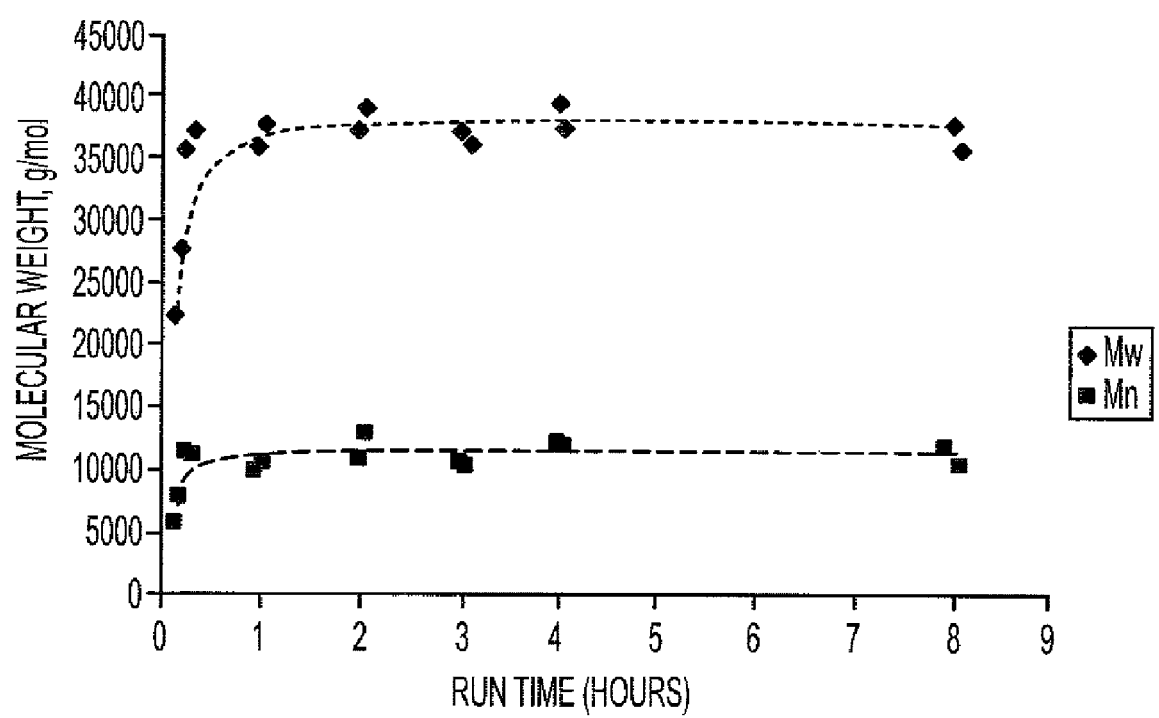
FIG. 4 shows polymer molecular weight as a function of polymerization run time for the exemplary polymerization of 11/12-pentadecen-15-olide and exaltolide, in accordance with various embodiments of the present teachings.

A 100-cm long segment of ¼-inch stainless steel tubing was capped at one end and filled with about 70 volume % of about 200-μm glass beads and 30 volume % (about 1 g) of Novozym® 435 (Novozymes, Denmark) to form the packed bed reactor. Novozym® 435 is an immobilized *Candida antarctica* lipase B resin. The contents of the packed bed reactor were equilibrated in toluene overnight to allow the resin to swell. After equilibration, inlet and outlet feed lines were attached to the packed bed reactor and the packed bed reactor was placed in a heating bath at about 80° C. About 625 ml of 30 wt. % monomer solution including a 1:1 mixture of 11/12-pentadecen-15-olide and pentadecalactone in toluene was pumped through the packed bed reactor continuously at a flow rate of about 1.3 ml/min. The product exiting the packed bed reactor was collected and analyzed using gel permeation chromatography (GPC) and differential scanning calorimetry (DSC). After about 30 minutes of operation, the molecular weight of the polymer in the outlet stream became stable ($M_n$=12-14 kg/mol), and the outlet stream was collected continuously for about 7.5 hours. The eluent was precipitated into methanol, and the resulting white solid was collected by filtration and air-dried, yielding about 180 g of crystalline polyester with $M_n$=13.6 kg/mol, $M_w$=36.2 kg/mol, PDI=2.66, and $T_M$=72° C. The overall conversion rate of monomer to polymer was calculated to be about 93%. The catalyst productivity under these conditions was about 180 g of polymer/g of catalyst which is approximately twenty times higher than that in a single batch experiment, as given below in Comparative Example 1. The true catalyst productivity in this reactor configuration is higher as the catalyst did not show signs of deactivation at the end of the production run, as the molecular weights remained unchanged, as shown in FIG. 4 and also the conversion rate was high, about 93 to about 95%.

Comparative Example 1

Polymerization of 11/12-pentadecen-15-olide and Pentadecalactone in a Batch Reactor About 1.5 g of 11/12-Pentadecen-15-olide and about 1.5 g of pentadecalactone were dissolved in about 3.5 ml toluene to which about 0.3 g of Novozym® 435 (Novozymes, Denmark) was added. The reaction mixture was stirred magnetically for about 4 hours at about 70° C., after that the reaction mixture became too viscous to stir. Upon cooling to room temperature, the reaction mixture crystallized to a wax-like solid, which was then re-dissolved in warm chloroform and filtered through glass wool. The Novozym® 435 beads were retained during filtration and were discarded. The filtrate was concentrated on a rotary evaporator to about 10 ml in volume. The concentrated solution was precipitated into methanol, and the resulting white solid was collected by filtration and air-dried, yielding about 2.47 g of crystalline polyester with $M_n$=11.6 kg/mol, $M_w$=53.4 kg/mol (PDI=4.59) and $T_M$=74° C. The overall conversion rate of monomer to polymer was calculated to be about 82%. The catalyst productivity for this batch was about 8 g of polymer/g of catalyst. If the catalyst can be recovered and recycled, higher catalyst productivities could be achieved in a batch process. However, it is unlikely that the catalyst productivities achieved in the packed bed reactor given in Example 1 could ever be achieved in a batch process due to catalyst deactivation and catalyst losses incurred through handling of the catalyst between batches.

Example 2

Bulk Polymerization of 11/12-pentadecen-15-olide and Pentadecalactone in a Continuous Packed-Bed Reactor A 10-cm long segment of ¼-inch stainless steel tubing was capped at one end and filled with about 70 volume % of about 200-μm glass beads and about 30 volume % (about 0.1 g) of Novozym® 435 (immobilized *Candida antarctica* lipase B resin) to form the packed bed reactor. The contents of the packed bed reactor were equilibrated in toluene overnight to allow the resin to swell. After equilibration, inlet and outlet feed lines were attached to the packed bed reactor and the packed bed reactor was placed in a heating bath at about 80° C. A bulk monomer solution comprised of a 1:1 mixture of 11/12-pentadecen-15-olide and pentadecalactone was pumped through the packed bed reactor continuously at a flow rate of about 0.13 ml/min. The product exiting the packed bed reactor was collected and analyzed using gel permeation chromatography (GPC). Under these conditions high molecular weight polymer with $M_n$=29,000 g/mol and $M_w$=74,000 g/mol (PDI=2.5) was produced without the need for solvent under bulk polymerization conditions.

Example 3

High Molecular Weight Polymers of 11/12-pentadecen-15-olide Produced in a Continuous Packed-Bed Reactor A 10-cm long segment of ¼-inch stainless steel tubing was capped at one end and filled with about 70 volume % of about 200-μm glass beads and about 30 volume % (about 0.1 g) of Novozym® 435 (immobilized *Candida antarctica* lipase B resin) to form the packed bed reactor. The contents of the packed bed reactor were equilibrated in toluene overnight to allow the resin to swell. After equilibration, inlet and outlet feed lines were attached to the packed bed reactor and the packed bed reactor was placed in a heating bath at about 80° C. A 50 wt. % monomer solution including 11/12-pentadecen-15-olide in toluene was pumped through the packed bed reactor continuously at a flow rate of about 0.13 ml/min. The eluent was precipitated into methanol, and the resulting white solid was collected by filtration and air-dried to yield a high molecular weight crystalline polyester with $M_n$=47,000 g/mol and $M_w$=133,000 g/mol, (PDI=2.83).

Example 4

Effect of Flow Rate on the Monomer Conversion of 11/12-pentadecen-15-olide, Polymer Molecular Weight and Polydispersity A 10-cm long segment of ⅜-inch stainless steel tubing was capped at one end and filled with about 70 volume % of about 200-μm glass beads and about 30 volume % (about 0.1 g) of Novozym® 435 (immobilized *Candida antarctica* lipase B resin) to form the packed bed reactor. The contents of the packed bed reactor were equilibrated in toluene overnight to allow the resin to swell. After equilibration, inlet and outlet feed lines were attached to the packed bed reactor and the packed bed reactor was placed in a heating bath at about 80° C. A 30 wt % monomer solution of 11/12-pentadecen-15-olide in toluene was pumped through the packed bed reactor continuously at varying flow rate in the range of about 0.01 ml/min to about 1 ml/min. The product exiting the packed bed reactor was collected and analyzed using gel permeation chromatography (GPC). For each flow rate a sample was collected following a period deemed to have been sufficient; about 18 to about 90 minutes depending on the flowrate. The eluent sample was precipitated into methanol, and the resulting white solid was collected by filtration and air-dried, yielding polymer with molecular weights in the range of about 15,000 g/mol ($M_n$) to about 30,000 g/mol ($M_n$) and about 40,000 g/mol ($M_w$) to about 60,000 g/mol ($M_w$) for the flow rate in the range of about 0.01 ml/min to about 1 ml/min. FIG. 2 shows the effect of flow rate on the monomer conversion and FIG. 3 shows the effect of flow rate on the polymer molecular weight and polydispersity.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a polyester comprising:
   providing a monomer solution, the monomer solution comprising one or more cyclic esters in a concentration ranging from about 1 to about 100% and one or more solvents in a concentration ranging from about 99% to about 0%;
   providing a packed-bed reactor comprising one or more immobilized enzymes, wherein the packed-bed reactor has an inlet and an outlet;
   circulating the monomer solution through the packed-bed reactor to generate a solution enriched with polyester, such that the one or more immobilized enzymes convert the one or more cyclic esters to polyester in the packed-bed reactor during circulation; and
   collecting the solution enriched with polyester exiting through the outlet.

2. The method of claim 1, where at least one of the one or more solvents is selected from the group consisting of toluene, benzene, hexane, heptane, tetrahydrofuran, and 2-methyltetrahydrofuran.

3. The method of claim 1, wherein the one or more cyclic esters comprises one or more 4 to 20 membered cyclic esters.

4. The method of claim 3, wherein the one or more cyclic esters comprises one or more of a pentadecalactone, a 11/12-pentadecen-15-olide, a hexadecenlactone, and a cap rolactone.

5. The method of claim 1, wherein at least one of the one or more enzymes is selected from the group consisting of lipase PA, lipase PC, lipase PF, lipase A, lipase CA, lipase B, lipase CC, lipase K, lipase MM, and cutinase.

6. The method of claim 1, wherein the packed-bed reactor further comprises one or more immobilizing agents.

7. The method of claim 6, where at least one of the one or more immobilizing agents is selected from the group consisting of a cross-linked polymeric network, cross-linked polymeric beads, polymeric packings, membranes, silica-gel, silica beads, sand, and zeolites.

8. The method of claim 6, wherein the packed-bed reactor has enzyme concentration ranging from about 0.001 $g/cm^3$ to about 0.06 $g/cm^3$.

9. The method of claim 6, wherein the packed-bed reactor is kept at a temperature from about 40° C. to about 100° C.

10. The method of claim 1, wherein the step of circulating the monomer solution through the packed-bed reactor to generate a solution enriched with polyester comprises passing the monomer solution through the packed bed reactor a plurality of times.

11. The method of claim 1 further comprising controlling one or more of molecular weight, polydispersity, and conversion ratio of the polyester using one or more of residence time of the one or more cyclic esters in the packed-bed reactor, dimensions of the packed-bed reactor, composition of the packed-bed reactor, temperature of the packed-bed reactor, and initiator concentration.

* * * * *